United States Patent [19]
Pirazzoli

[11] Patent Number: 5,401,238
[45] Date of Patent: Mar. 28, 1995

[54] METHOD OF MONITORING A DIALYSIS UNIT

[75] Inventor: Paolo Pirazzoli, Modena, Italy

[73] Assignee: Hospal, Ltd., Switzerland

[21] Appl. No.: 982,747

[22] PCT Filed: Jul. 16, 1992

[86] PCT No.: PCT/EP92/01543
§ 371 Date: May 6, 1993
§ 102(e) Date: May 6, 1993

[87] PCT Pub. No.: WO93/01845
PCT Pub. Date: Feb. 4, 1993

[30] Foreign Application Priority Data
Jul. 16, 1991 [IT] Italy ................. 91A000560

[51] Int. Cl.⁶ .............................................. A61M 1/16
[52] U.S. Cl. .......................................... 604/4; 604/65; 210/646
[58] Field of Search .............. 128/630; 604/4–6, 604/65, 66, 27–31; 210/646, 647, 321.71

[56] References Cited
U.S. PATENT DOCUMENTS
4,601,830  7/1986  Chen .................... 210/647

FOREIGN PATENT DOCUMENTS
9014850  12/1990  WIPO .................... 210/646

*Primary Examiner*—Kyle L. Howell
*Assistant Examiner*—Robert L. Nasser
*Attorney, Agent, or Firm*—Finnegan, Henderson, Farabow, Garrett, & Dunner

[57] ABSTRACT

The monitoring method comprises the stages of acquiring and storing the values ($Q_{inf}$, $Q_b$ and $Q_{UF}$) of a plurality of parameters set by the operator for the individual dialysis treatment to be carried out and for determining the doctor's clinical prescription $[[HCO_3^-]_b]$ on the basis of the stored values of the parameters prior to the commencement of treatment. During the dialysis treatment, the current values ($Q_{infl}$, $Q_{b1}$ and $Q_{UF1}$) of the parameters set are continuously acquired (block 29) and if these current values differ significantly from the stored values or in such a way as to entail a change to the predetermined prescription, an alarm signal (36) is generated and a new value ($Q_{infs}$) for some parameters calculated in advance (block 31) is suggested so as to maintain the previous prescription unchanged.

11 Claims, 3 Drawing Sheets

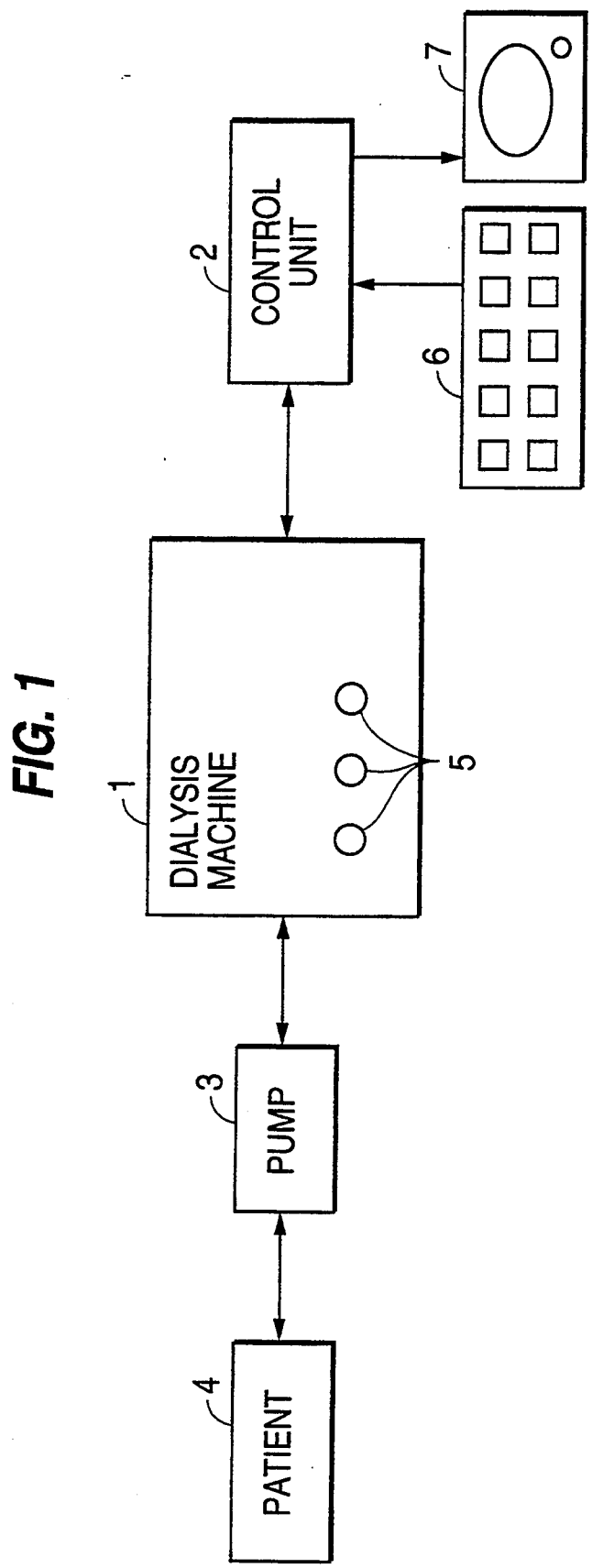

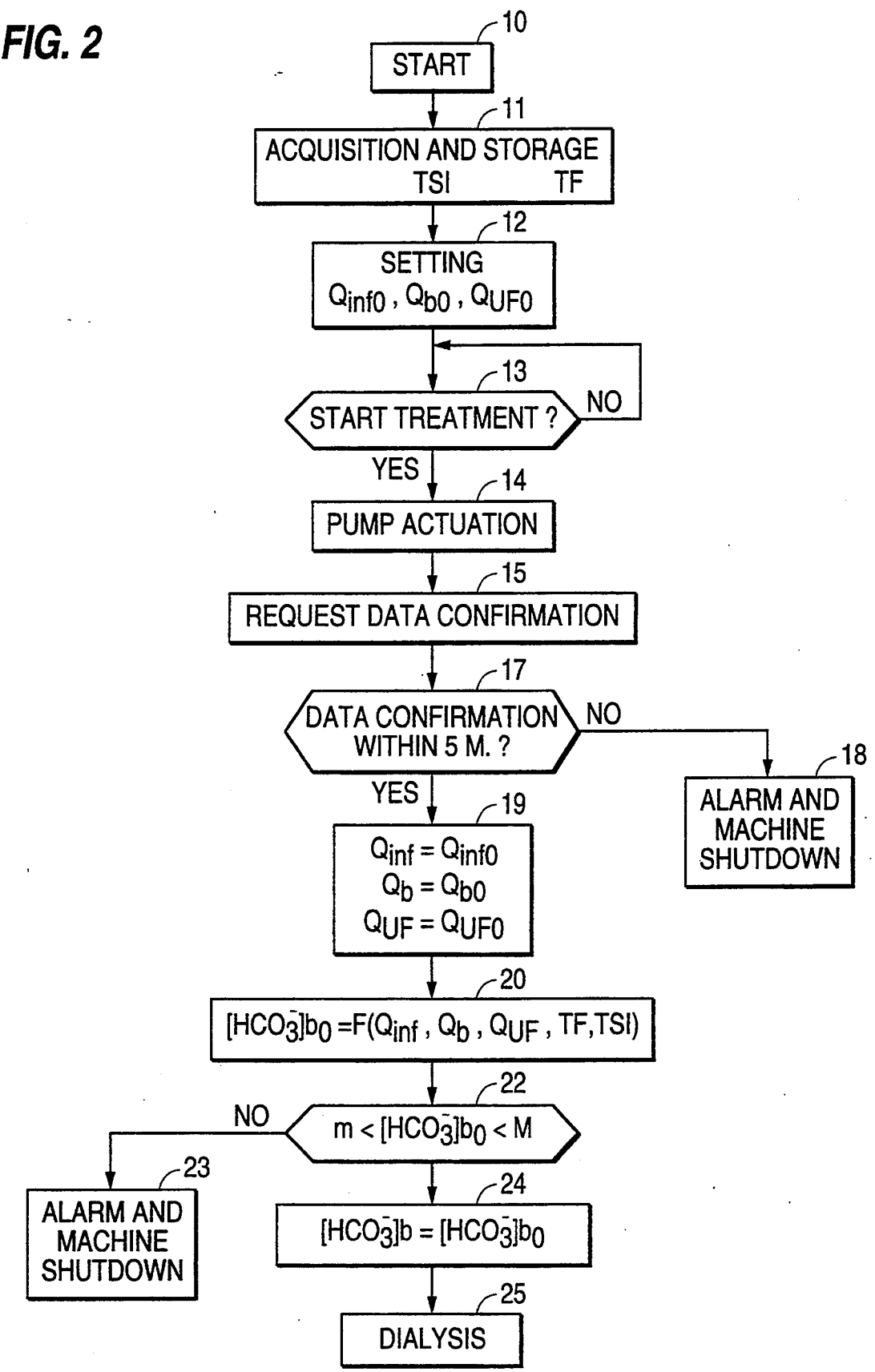

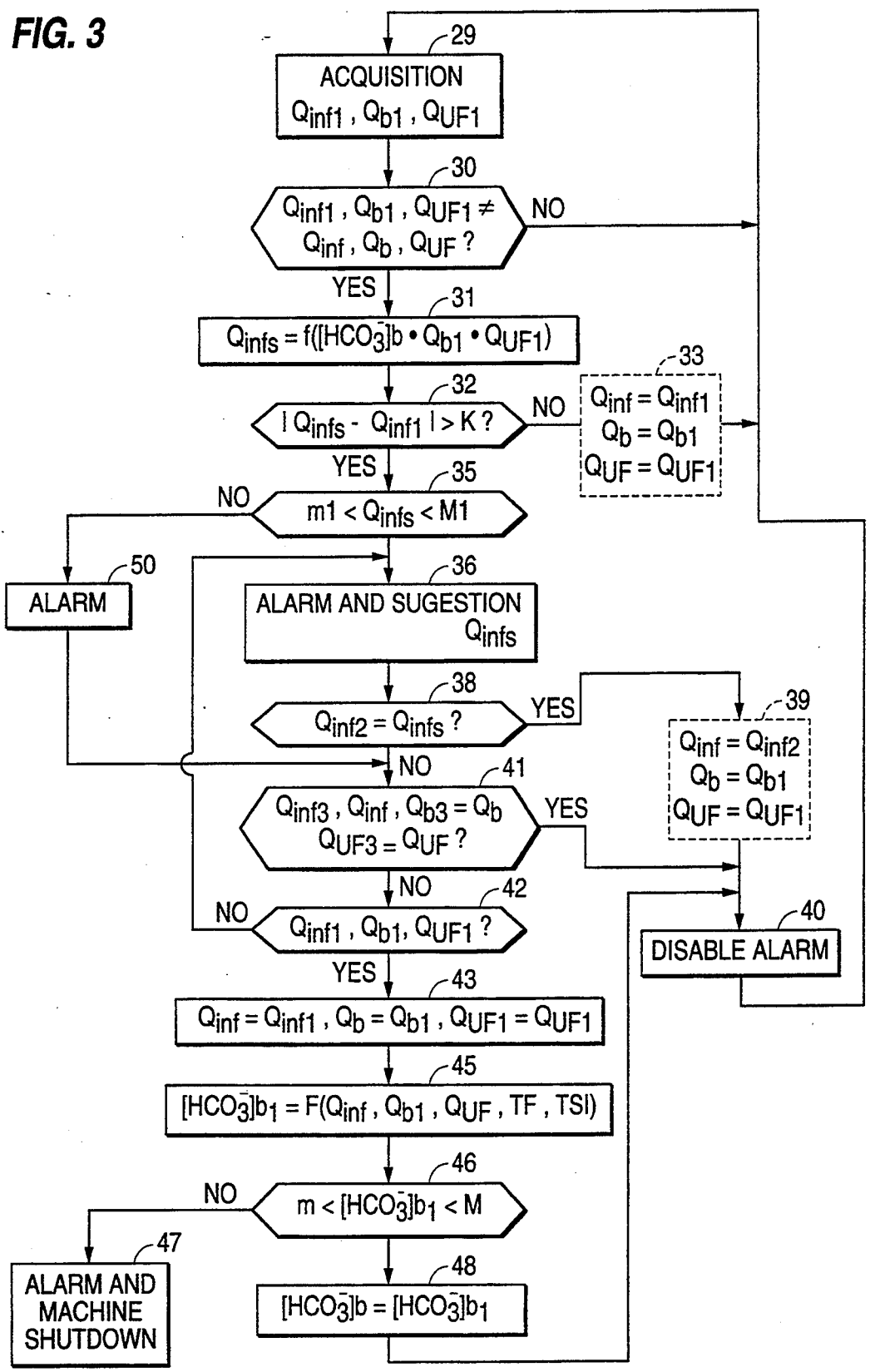

METHOD OF MONITORING A DIALYSIS UNIT

BACKGROUND OF THE INVENTION

1. Field of the Invention

The present invention relates to a method of monitoring a dialysis unit, and has particular application to "acetate free" treatment.

2. Description of the Related Art

As is known, when a doctor prescribes a specific dialysis treatment, he indicates the value of certain parameters which must be set by the operator on the dialysis machine prior to starting the treatment. In practice, the values of the parameters to be set are correlated unambiguously with one or more variables whose control forms the objective of the treatment. For instance, in case of "acetate free" treatment there are five parameters to be set, i.e. type of filter used, type of infusion pack used (supplied as bicarbonate concentration in the infusion pack), blood flow, infusion rate and ultrafiltration rate (supplied as a weight loss) and their value in practice determines the desired bicarbonataemia in the blood in a stable condition.

In these conditions, alteration by the operator of one of the treatment parameters (in particular the last three, bearing in mind that the type of filter and the type of pack used cannot in theory be modified during the actual treatment) generally causes a variation of the bicarbonataemia and therefore a modification of the prescription which may in some cases, if not controlled, place the patient at risk. Such risk includes reduction in blood flow or even its stoppage which in turn may lead in to alkalosis.

Although mathematical models which provide the relationship existing between the treatment parameters set by the operator and the variable formed by the doctor's prescription are currently available, known machines do not in general provide for any control of this variable with the result that it is impossible to avoid risk situations.

SUMMARY OF THE INVENTION

The object of the present invention is therefore to provide a method for monitoring a dialysis unit which allows the operator to avoid potential risk situations.

According to the present invention, a method of monitoring a dialysis unit is provided which comprises the stages of acquiring and storing set values of a plurality of parameters relating to the treatment to be carried out, characterized in that it comprises the determination of a clinical prescription on the basis of the stored values of the parameters, the detection of variations in the set values of these parameters, the detection of any variation in the prescription due to these variations in the set values and the generation of an alarm signal if this variation in the prescription is detected.

In practice, the method of the invention provides that, at the beginning of treatment, the control unit of the dialysis machine calculates the desired prescription on the basis of the set values of the parameters and a mathematical model which links these parameters to a variable defining the prescription and then, for any maneuver by the operator causing a variation of the prescription, generates an alarm signal for the operator. This alarm signal is preferably accompanied by the suggestion of new values for some of the parameters so as to maintain the previous prescription, the operator being able to choose between three actions: resetting the previous value of the parameters, setting the suggested value of the parameters or confirming the new values which have just been set and thus updating the prescription correspondingly.

BRIEF DESCRIPTION OF THE DRAWINGS

The present invention is described in detail with respect to a preferred embodiment, given purely by way of non-limiting example, made with reference to the accompanying drawings, in which:

FIG. 1 is a block diagram of the system to which the present method is applied; and FIGS. 2 and 3 show two flow charts relating to an "acetate free" treatment method of the invention.

DESCRIPTION OF THE PREFERRED EMBODIMENTS

In FIG. 1, the method of the invention is applied to a system comprising, in outline, a dialysis machine 1 connected to a control unit 2 and, via an extracorporeal circulation system comprising a peristaltic pump 3, to a patient 4. The machine 1 has a plurality of knobs 5 for setting certain parameters relating to the dialysis treatment, while the control unit 2 is connected to a keyboard 6 and a monitor 7 for the exchange of information and instructions with the operator. The control unit 2 (which may also be inside the machine 1 in the same way as the peristaltic pump 3, the keyboard 6 and the monitor 7) controls the operation of the machine 1, supplying it with the information needed to carry out the prescribed dialysis treatment and is also adapted to monitor any variations in the parameters entailing a change to the prescription, according to the method described below with reference to FIGS. 2 and 3.

In FIG. 2, the treatment starts (block 10) when the operator (nurse) sets an "acetate free" treatment on the machine. The control unit 2, via the screen 7, then requires the operator to set the type of filter (TF) and the type of infusion pack (TSI, which is supplied as bicarbonate concentration in the pack). These values are keyed in via the keyboard 6 and are then stored (block 11). Prior to the commencement of the treatment and in a known manner, for instance using the knobs 5, the operator sets the initial values (called $Q_{info}$, $Q_{bO}$ and $Q_{UFO}$) of the infusion rate, blood flow and ultrafiltration rate (usually supplied as WLR—Weight Loss Rate) (block 12). The control unit 2 then waits (block 13) for the operator to start the treatment, after which it controls the actuation of the peristaltic pump 3 (block 14) and requests confirmation of the data set (block 15).

According to the present method, the unit 2 waits for this confirmation for a predetermined time, for instance 5 minutes. If the operator does not confirm the data within this period (output NO from block 17) the treatment is interrupted, the pump 3 is stopped and an alarm signal is generated (block 18). In the opposite case (output YES from block 17), the unit 2 stores the infusion, blood and ultrafiltration rates (block 19) and calculates the initial value of the bicarbonataemia $[HCO_3^-]_{b0}$ (block 20) on the basis of a stored mathematical model using as input variables the five parameters set and a standard value of the patient's haematocrit (as an alternative, the patient's haematocrit value may be set by the operator via the keyboard as described with respect to block 11 for the parameters TF and TSI).

The bicarbonataemia value $[HCO_3^-]_{b0}$ set in this way is compared with a lower threshold m and an upper threshold M to check that it comes within a correct interval (block 22) and if it does not come within the interval defined by these upper and lower thresholds (output NO from block 22) there is a transition to block 23 where an optical and/or acoustic alarm is generated and the machine is stopped. If the bicarbonataemia value calculated comes within this interval, this value is stored as a current value $[HCO_3^-]_b$ (block 24), is possibly displayed and the machine starts the dialysis (block 25) on the basis of the parameters specified by the operator.

During the dialysis (see FIG. 3) the present method provides for the checking, either continuously or at predetermined time intervals, of any change to those parameters which may be modified (i.e. Qinf, $Q_b$ and $Q_{UF}$). For this purpose, the current values $Q_{inf1}$, $Q_{b1}$ and $Q_{UF1}$, set by the knobs 5, of the parameters which may be modified are acquired (block 29) and these current values are compared with the stored values (block 30). If they tally (output NO from block 30), the dialysis continues in the manner set previously and monitoring is continued, returning to block 29. If, however, it is detected that at least one of the parameters has changed (at least one of the values $Q_{inf1}$, $Q_{b1}$ and $Q_{UF1}$ detected at that moment differs from the stored values $Q_{inf}$, $Q_b$ and $Q_{UF}$), there is a transition from block 30 to block 31 where a new value is calculated for the suggested infusion rate $Q_{infs}$, as a function of the bicarbonataemia previously calculated and stored and the current values $Q_{b1}$ and $Q_{UF1}$ of the blood flow and ultrafiltration rate. In practice, when the unit 2 detects a modification of one or more of the parameters, it calculates a new value for the infusion rate so as to maintain the bicarbonataemia value at the previously stored value.

The suggested value of the infusion rate $Q_{infs}$ is then compared with the value which has just been detected (block 32); if the difference between the two is lower than a predetermined value K (for instance 10 ml/h), i.e the modification of the parameters is not significant (small variation of the parameters which does not entail changes to the prescription) or the new values set for the parameters do not entail a modification of the prescription (the values of the parameters have been modified in a targeted way in order to maintain the bicarbonataemia value unchanged) there is a transition from block 32 to block 33 in which the values currently set for the parameters $Q_{inf1}$, $Q_{b1}$ and $Q_{UF1}$ are stored in place of the previous values (even if they partially coincide with these) and there is a return to block 29.

In contrast, if the modification of at least one parameter entails a re-adjustment of the infusion rate to maintain the same prescription, the new value suggested for the infusion rate is compared with a minimum threshold m1 and a maximum threshold M1 (block 35). If the new suggested value $Q_{infs}$ is within the interval defined by these thresholds (output YES from block 35), there is a transition to block 36 in which the unit 2 generates an alarm which warns the operator that the maneuver which has just been performed is not in accordance with the previous prescription, possibly displays the values of the parameters prior to the maneuver which has just been made and suggests the suggested value of the infusion rate which has just been calculated $Q_{infs}$. At this stage, the operator has three options: i.e to modify (or re-modify) the value of the infusion rate on the basis of the suggested value in order to maintain the prescribed bicarbonataemia, to cancel out the modifications which have been made and reset the previous values of the parameters or to confirm the values which have just been modified and consequently also to modify the prescription (bicarbonataemia). These options are shown in the Figure by the interrogation blocks 38, 41 and 42.

If the operator decides to take up the suggestion made by the unit 2 and sets a new value for the infusion rate $Q_{inf2}$ equivalent to the suggested value $Q_{infs}$ (output YES from block 38), the current values of the parameters are stored in place of the previous values (block 39), the alarm is disabled (block 40) and there is a return to block 29 continuing the dialysis with the values which have just been set which do not in any case entail a modification of the prescription.

If the operator decides, however, to reset the previous values of the parameters, cancelling the maneuver performed previously (output NO from block 38 and output YES from block 41), there is a direct transition to block 40 for the disabling of the alarm and the dialysis continues exactly as before, prior to the maneuver to modify the parameters.

If the operator decides, however, to confirm the modifications of the parameters made, he informs the unit 2 of this decision by pressing an appropriate key and there is a transition from block 42 to block 43 for the storage of the values set. Consequently the values $Q_{inf1}$, $Q_{b1}$ and $Q_{UF1}$ are written over the previous values and are used for the subsequent control of the dialysis. The new value of the bicarbonataemia $[HCO_3^-]_{b1}$, corresponding to the new value of the parameters is then calculated (block 45), checking takes place to ascertain that this new value comes within the predetermined admissibility interval (block 46) and if not an alarm signal is generated and the machine is stopped (block 47). If, however, the new value of the bicarbonataemia is admissible it is stored in place of the previous value (block 48), the alarm is disabled (block 40) and a return is made to block 29.

If, following the alarm signal due to a variation of at least one of the parameters likely to entail a variation of the prescription, the operator does not choose any of the three options provided (output NO from block 42), the alarm continues (as shown in the Figure by the return to block 36). If, following a significant variation of one of the parameters, the new value calculated for the infusion rate does not come within the predetermined admissibility interval (output NO from block 35), the operator has only two options: to reset the previous values of the parameters or to confirm the modified values, at the same time modifying the prescription. This entails the generation of a specific alarm and the display of the previous values of the parameters (block 50), obviously without displaying the suggested value and without offering the possibility of setting this suggested value. The stages shown by blocks 36 and 38 are consequently skipped and there is a direct transition from block 50 to block 41.

The method of the invention has the following advantages. In the first place it makes it possible to show all situations of potential risk since it is able to reconstruct the doctor's prescription on the basis of the values of the parameters set and thus to recognize the effects of any maneuver entailing a variation of the parameters during the treatment. In this way it is consequently possible to predict conditions which are dangerous for the patient before they arise and to inform the operator thereof or even to stop the machine, thereby preventing these situations.

With the present method it is also possible to monitor the operator's actions and generate alarm signals whenever these actions entail a variation in the previously set prescription, while allowing the operator to confirm the choices made when these correspond to actual clinical needs. This method also makes it possible to make small adjustments to the treatment so as to bring some local parameters into line with specific clinical conditions, without modifying the prescription, since it is possible to calculate and suggest the value of some parameters (the infusion rate in this case) which make it possible to maintain the prescription with new values for certain parameters (the blood flow and ultrafiltration rate in this case). In general, this possibility may require the definition of certain hierarchically superior (or control) parameters and certain hierarchically inferior (or controlled) parameters with the result that the modification of the value of the control parameters entails an adjustment of the value of the controlled parameters in order to maintain the doctor's prescription unchanged.

It is evident that modifications and variants which do not depart from the scope of the invention may be made to the method described and illustrated. It is stressed in particular that, although the particular case of "acetate free" treatment has been described, the same solution may be applied to other dialysis treatments, in which case the parameters of the machine to be set and/or the variable represented by the prescription are varied. In certain cases it is also possible to reduce or extend the alternatives open to the operator in the case of variation of some parameters, for instance in the case where the variable defining the prescription must not be changed in any way during the treatment or where the modification of some parameters entails specific operations or action by the machine or the operator. In particular, instead of simply suggesting new calculated values for the controlled parameters when some control parameters are modified, the method may comprise the automatic setting of these new calculated values. In the case of the "acetate free" treatment described, the parameters may be subject to other controls: provision may, for instance, be made for the generation of a specific alarm signal if the operator attempts to modify one of the parameters which cannot be modified such as the type of filter or infusion pack, or, when solely the infusion rate (or the controlled parameter in general), is modified, for the user to be provided with the sole choice of resetting the previous value without the possibility of modifying the prescription. In the treatment described, the values resulting from changes to the parameters which do not entail the variation of the prescription (and are not therefore explicitly confirmed by the operator) may also not be stored; in this case the blocks 33 and 39 are not provided.

What is claimed is:

1. A dialysis treatment method comprising the steps of:
    conducting blood through a blood side of a dialysis unit during a treatment session;
    withdrawing a used fluid from a used fluid side of the dialysis unit during the treatment session;
    storing in a first memory location desired values for a plurality of treatment parameters relating to a treatment to be carried out by the dialysis unit, at least one of the plurality of parameters being a controlled parameter having an initial value, the plurality of treatment parameters corresponding to a desired clinical prescription;
    detecting, during the treatment session, current values of said plurality of treatment parameters;
    comparing the current values with the stored desired values;
    calculating a suggested value of the controlled parameter to maintain the clinical prescription when at least one of the current parameter values differs from a corresponding desired value;
    comparing the suggested value of the controlled parameter with the initial value of the controlled parameter to determine a difference;
    determining whether the suggested value of the controlled parameter falls within a threshold range when an absolute value of the difference is greater than a predetermined value; and
    generating a warning signal indicating that the current values are not in accordance with the desired clinical prescription when the suggested value of the controlled parameter falls outside of the threshold range.

2. A method according to claim 1, further comprising the step of replacing in the first memory location the desired values of the treatment parameters with the current values when said difference is lower than a predetermined threshold.

3. A method according to claim 1, further comprising the step of generating an alarm signal and displaying the suggested value of the controlled parameter when the suggested value of the controlled parameter falls within the threshold range.

4. A method according to claim 3, further comprising the steps of obtaining a current value of the controlled parameter, comparing the current value with the suggested value, storing the current value in memory and disabling the alarm signal if the current value is identical to the suggested value.

5. A method according to claim 3, further comprising the steps of obtaining new current values of the treatment parameters, comparing the new values with the desired values stored in the first memory location, and disabling the alarm signal when the new current values are substantially the same as the stored values.

6. A method according to claim 5, further comprising the steps of detecting a confirmation signal of the current values, calculating a new value for the desired clinical prescription based on the new parameter values, storing the current parameter values and the new desired clinical prescription in memory, and disabling the alarm.

7. A method according to claim 1, wherein the desired values of the parameters are related to the desired clinical prescription by a mathematical model, the desired values of the parameters being input variables of the mathematical model and the desired clinical prescription being an output value of the mathematical model, the method further comprising the step of storing the output value in a second memory location.

8. A method according to claim 7 wherein the treatment parameters include both control parameters and controlled parameters, and wherein the step of calculating a suggested value for at least the controlled parameter includes calculating a suggested value based on a current value of at least one control parameter and a value of the desired clinical prescription stored in said second memory location.

9. A method according to claim 8 wherein the control parameters include blood flow and ultrafiltration rate, the controlled parameters includes infusion rate and the clinical prescription include bicarbonataemia.

10. A dialysis treatment method comprising the steps of:

storing in a first memory location desired values for a plurality of treatment parameters relating to a treatment to be carried out, at least one of the plurality of parameters being a controlled parameter having an initial value, the plurality of treatment parameters corresponding to a desired clinical prescription;

detecting, during a treatment session, current values of said plurality of treatment parameters;

comparing the current values with the stored desired values;

calculating a suggested value of the controlled parameter to maintain the clinical prescription when at least one of the current parameter values differs from a corresponding desired value;

comparing the suggested value of the controlled parameter with the initial value of the controlled parameter to determine a difference;

determining whether the suggested value of the controlled parameter falls within a threshold range when an absolute value of the difference is greater than a predetermined value;

generating a warning signal indicating that the current values are not in accordance with the desired clinical prescription when the suggested value of the controlled parameter falls outside of the threshold range; and adjusting the controlled parameter to substantially maintain the desired clinical prescription by replacing the initial value of the controlled parameter with the suggested value of the controlled parameter when the suggested value of the controlled parameter falls within the threshold range.

11. A dialysis treatment method comprising the steps of:

conducting blood through a blood side of a dialysis unit during a treatment session;

withdrawing a used fluid from a used fluid side of the dialysis unit during the treatment session;

storing in a first memory location desired values for a plurality of dialysis treatment parameters relating to a treatment to be carried out by the dialysis unit during the treatment session, at least one of the plurality of parameters being a controlled parameter having an initial value, the plurality of dialysis treatment parameters corresponding to a desired clinical prescription;

detecting, during the treatment session using the dialysis unit, current values of said plurality of dialysis treatment parameters;

comparing the current values with the stored desired values;

calculating a suggested value of the controlled parameter to maintain the clinical prescription when at least one of the current parameter values differs from a corresponding desired value;

comparing the suggested value of the controlled parameter with the initial value of the controlled parameter to determine a difference;

determining whether the suggested value of the controlled parameter falls within a threshold range when an absolute value of the difference is greater than a predetermined value;

generating a warning signal indicating that the current values are not in accordance with the desired clinical prescription when the suggested value of the controlled parameter falls outside of the threshold range; and adjusting the controlled parameter to substantially maintain the desired clinical prescription by replacing the initial value of the controlled parameter with the suggested value of the controlled parameter when the suggested value of the controlled parameter falls within the threshold range.

* * * * *